(12) United States Patent
Wilbur et al.

(10) Patent No.: US 6,180,000 B1
(45) Date of Patent: Jan. 30, 2001

(54) SURGICAL WASTE LIQUID AND SMOKE DISPOSAL SYSTEM

(75) Inventors: Lawrason C. Wilbur, Lake Forest; Peter Regla, Placentia; William M. Doran, Costa Mesa; Phillip C. Darling, Jr., Fullerton, all of CA (US)

(73) Assignee: American Immuno Tech, LLC, Costa Mesa, CA (US)

( * ) Notice: Under 35 U.S.C. 154(b), the term of this patent shall be extended for 0 days.

(21) Appl. No.: 09/375,228

(22) Filed: Aug. 16, 1999

Related U.S. Application Data

(62) Division of application No. 09/042,551, filed on Mar. 17, 1998, now Pat. No. 5,997,733.

(51) Int. Cl.[7] ............................................. B01D 17/12
(52) U.S. Cl. ........................... 210/85; 55/467.1; 210/143; 210/175; 210/258; 340/664; 422/169; 604/319; 606/45
(58) Field of Search ........................ 210/85, 143, 149, 210/175, 180, 182, 188, 241, 257.1, 258, 259; 604/317, 319, 322; 606/45; 422/1, 4, 169; 55/467, 467.1, 356

(56) References Cited
U.S. PATENT DOCUMENTS

| | | | |
|---|---|---|---|
| 4,921,679 | * | 5/1990 | Martin et al. ........................ 422/169 |
| 4,963,134 | * | 10/1990 | Backsheider et al. ............... 604/319 |
| 5,234,419 | * | 8/1993 | Bryant et al. ........................ 604/319 |
| 5,318,516 | * | 6/1994 | Cosmescu .............................. 606/45 |
| 5,520,668 | * | 5/1996 | Greffa et al. ......................... 604/319 |
| 5,522,808 | * | 6/1996 | Skalla ................................... 604/319 |
| 5,607,411 | * | 3/1997 | Heironimus et al. ................ 604/319 |
| 5,910,291 | * | 6/1999 | Skalla et al. ......................... 422/169 |
| 5,914,047 | * | 6/1999 | Griffiths .............................. 604/319 |
| 5,945,004 | * | 8/1999 | Ohira et al. .......................... 210/258 |

* cited by examiner

Primary Examiner—Joseph W. Drodge
(74) Attorney, Agent, or Firm—G. Donald Weber, Jr.

(57) ABSTRACT

A waste liquid and smoke disposal system which combines the functions of a smoke extraction system and a waste (typically, liquid) collection system, typically in, but not limited to, a surgical environment. The smoke extraction system and the liquid waste collection system are connected to supply the waste materials collected thereby to a waste treatment (e.g. decontamination and/or sterilization) and disposal system. In a preferred embodiment, the waste treatment system includes a plurality of heat exchanger units for efficient controlling of the temperature of the waste material during the waste treatment process. These three systems are all combined into a integrated system wherein the treated waste can be safely returned to the ambient. In one embodiment, the system is provided as a cart-mounted apparatus to provide mobility.

20 Claims, 5 Drawing Sheets

SURGICAL WASTE LIQUID AND SMOKE DISPOSAL SYSTEM

This is a division of application Ser. No. 09/042,551, filed Mar. 17, 1998, now U.S. Pat. No. 5,997,733.

BACKGROUND

1. Field of the Invention

This invention is directed to a medical waste collection and treatment system, in general, and to such a system which is integrated into a unitary mobile system, in particular.

2. Prior Art

During a surgical procedure, the surgical site on a patient may undergo several protocols including, for example, a cauterizing procedure. Cauterizing generates smoke containing foul smelling volatiles and potentially infectious airborne particles. For sanitary reasons, this smoke must be removed, especially from the volume of air immediately surrounding the cauterizing site.

While removing the cautery-generated smoke, it is typical and frequent that other detritus, effluent or the like is removed, as well. This material, generically referred to as "waste material", is frequently contaminated and/or toxic.

In this day and age, it is highly environmentally sensitive and/or politically correct to dispose of this waste material in a non-polluting manner. The definition of non-polluting, in this context, is highly sensitive, as well. Consequently, it is necessary to use extremely careful techniques and protocols to dispose of such waste materials.

SUMMARY OF THE INSTANT INVENTION

The mobile surgical waste liquid and smoke disposal system of the instant invention combines the functions of a smoke extraction system (especially for removing smoke generated during a cauterization procedure), a liquid waste collection system for collecting liquid waste or effluent from a surgical site, and a liquid waste treatment (i.e. decontamination and/or sterilization) and disposal system into a unitary, integrated and mobile (e.g. cart-mounted) system. This system permits the surgical team to quickly, easily and efficiently maintain the integrity of a surgical site with a minimum of operating components. The mobility thereof permits the system to be located (and relocated) with ease and efficiency. By treating the waste matter with the disposal apparatus of the invention, ready and safe disposal of the waste matter is achieved.

DESCRIPTION OF A PREFERRED EMBODIMENT

Figure 1:
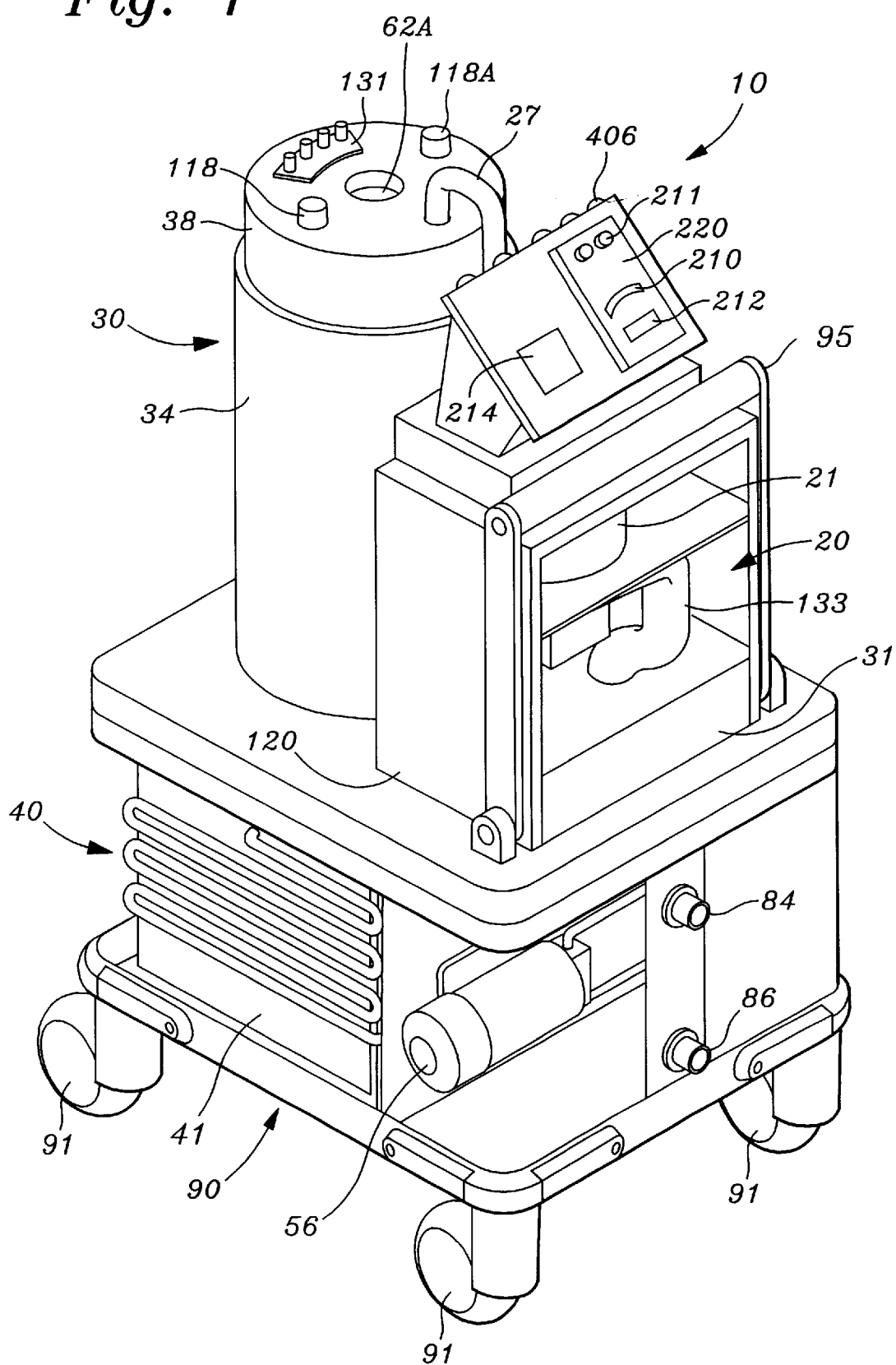
FIG. 1 is a pictorial representation of the apparatus of the instant invention.

Referring now to FIG. 1, there is shown an external perspective representation of a mobile surgical waste liquid and smoke disposal and/or treatment system apparatus 10. The apparatus 10 combines the functions of a smoke extraction system 20, a liquid waste collection system 30, and a liquid waste treatment (i.e. decontamination or sterilization) and disposal system 40 into an integrated system. These components are described in detail infra.

In the preferred embodiment, the apparatus 10 includes a cart 90 with suitable wheels 91 to provide mobility for the apparatus and includes a handle 95 which is pivotally mounted to the apparatus to facilitate movement of the cart 90 and the apparatus mounted thereon.

In a preferred embodiment, the treatment and disposal system 40 includes a heat exchanger in which waste materials are heated to a predetermined temperature for a prescribed duration. A water inlet 84 is connected to the heat exchanger system 41 as is the waste outlet 86. The pump 56 selectively moves material from waste collection system 30 to the waste treatment system 40. A non-sterile output is also provided.

The liquid waste collection system 30 includes a mounting cylinder 34 surmounted by a cap 38. The cap 38 includes an aperture 62A which is used for insertion of a cleaning spray tube (described infra). The cap 38 also includes ports 118 and 118A which are selectively connected to cauterization instruments or the like.

In addition, a multi-port manifold 131 is provided in cap 38 in order to selectively connect to additional equipment such as, but not limited to, lavage devices, suction tubes or the like.

A tower housing 120 supports the smoke extraction system 20 and the control panel 220. The system 20 includes a fan or blower unit housing 21 and a smoke exhaust tube 133. The smoke exhaust tube 133 connects the smoke extraction system 20 to the smoke exhaust described infra. The air tube 27 is connected from the cap 38 to the blower system 20 (as shown in greater detail in FIG. 3). The control panel 220 includes a suitable display 210 which shows the speed of operation of the blower in the blower housing 21 which represents the amount of vacuum in the smoke extractor 20. In one embodiment, control knobs 211 (and others if desired) can be provided to control the speed of the blower.

In addition, an appropriate ambient light sensor 212 as well as IR signal detectors 406 (described infra) can be placed at convenient locations on the control panel along with a conventional power switch 214.

Figure 2:
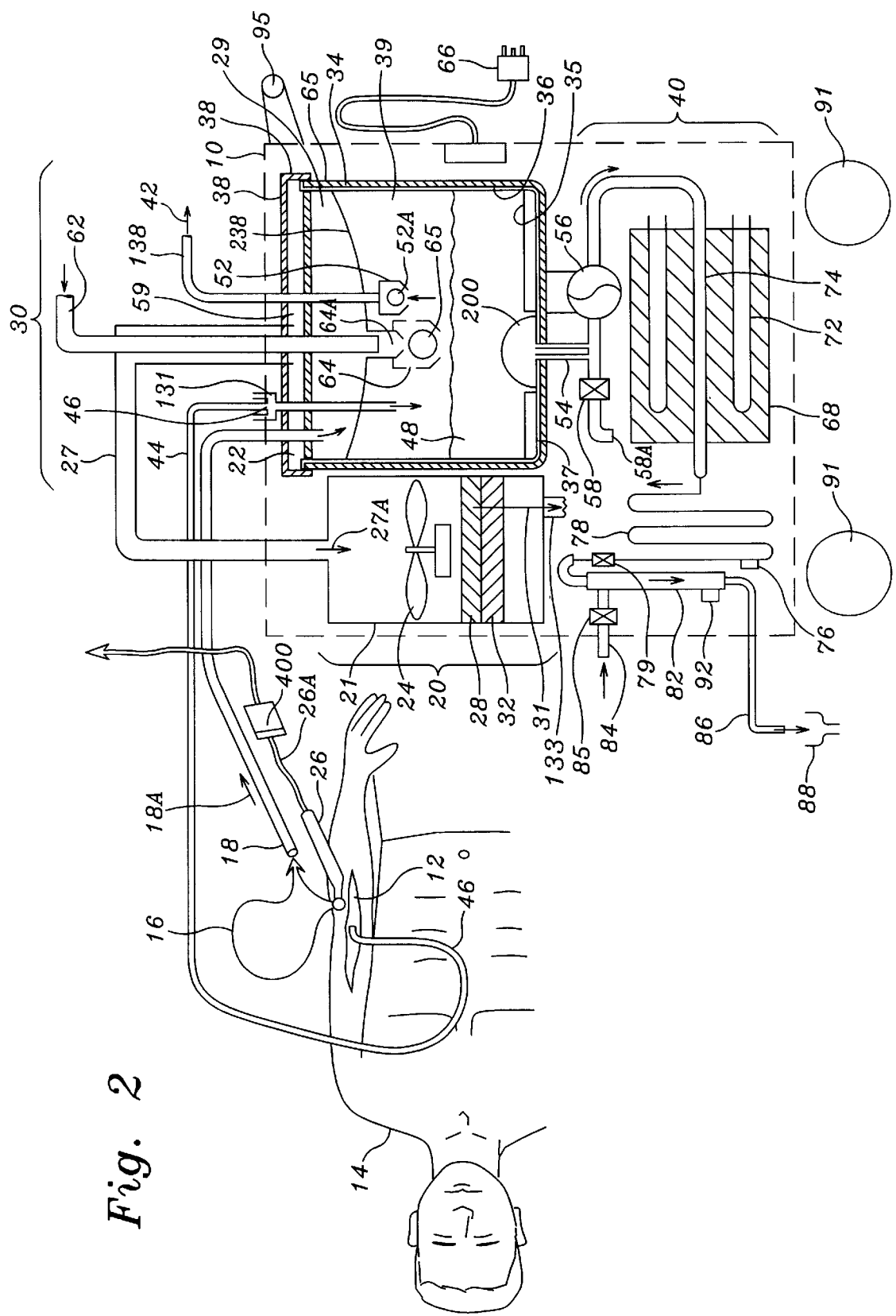
FIG. 2 is a schematic representation of several components of the apparatus of the instant invention.

Referring now to FIG. 2, there is shown a more detailed schematic representation of the smoke extraction system 20, liquid waste collector 30 and the treatment/disposal system 40 of the apparatus 10.

Typically, a patient 14 with a surgical site 12 may undergo a cauterizing procedure. The smoke generated during this procedure, typically, contains foul smelling volatiles and potentially infectious airborne particles which must be removed from the volume of air immediately surrounding the cauterizing site. This removal is accomplished by the smoke extraction system 20.

The system 20 includes a fan housing 21 and a fan 24 mounted therein. The fan 24 is, typically, designed to operate at a relatively low speed in the normal or standby mode. However, when cautery instrument 26 is turned ON, fan 24 is switched from the low standby speed to a relatively high speed by an IR current sensor switch 400 shown schematically and described in greater detail relative to FIG. 3.

The high speed operation of fan 24 establishes air flow through tube 27 which is joined to the housing 21. The air flow is in the direction shown by the arrow 27A. This air flow creates a suitable vacuum in inlet chambers 29 and 59 formed under cap 38 by filter separator 22. (See FIG. 6 for details.) In particular, the fan 24 (or blower) runs at a sufficiently high speed to create a vacuum, typically on the order of −9 in. of Hg (maximum) in this embodiment. The air flow from chamber 29 (created by fan 24 in housing 21) passes through filter 22 which is disposed between chambers 59 and 29 in cap 38. In this embodiment, filter 22 filters out particulates greater than about 10 micron and serves to protect fan 24.

The vacuum in chamber 29 induces the flow of smoke from surgical site 12 via tube 18 into chamber 29, chamber 59 and, thence, through tube 27 to blower 24. A 10 micron pre-filter 22 separates chambers 29 and 59 of cover 38 to remove large particulates from the flow of smoke to blower 24.

As cauterizing smoke is captured by the smoke extraction system 20, it is conducted through tube 18 to chamber 29. From there the air flow passes across (or through) filter element 22 to chamber 59 and is, thence, conducted through tube 27, as described supra. The air flow passes from tube 27 through blower 24.

The smoke flows through blower 24 thence through high efficiency filter 28 which removes particulates down to 0.2 microns. The smoke continues through activated carbon filter 32 which adsorbs volatile organic molecules and compounds responsible for objectionable odors. This combined filtration renders exhaust air (indicated by arrow 31) essentially particle and odor free. Exhaust air 31 is then directed via exhaust tube 133 around various system components that require cooling and is, ultimately, released to the atmosphere.

As suggested supra, during cauterizing, some liquid from the wound site 12 can be drawn into chamber 29. For example, liquid droplets and vapor entrained in the smoke 16 during cauterizing condense and collect in chamber 29. However, during cauterizing, the pressure in chamber 29 is lower than the pressure in the collection container 39, as described supra. This pressure imbalance forces ball 65 upwardly, thereby sealing the opening 64 in filter separator 22 and closing the passage between chamber 29 and collection chamber 39.

When cautery instrument 26 is turned OFF, blower 24 switches back to low speed to provide cooling air for other system components through appropriately located air flow orifices. When the cauterizer is turned off, the pressure in chamber 29 exceeds the pressure in container 39 (i.e. the chamber below the filter separator). This pressure imbalance forces ball 65 downwardly and allows any liquid in chamber 29 to drain into the collection chamber 39 of container 34 of the liquid waste collection system 30 described infra.

Vacuum or connector tube 42 is connected to the existing conventional vacuum system in the operating room (or other facility). The available vacuum of approximately −2 inches of Hg is conducted through tank cover 38 and is metered through an input orifice such as at manifold 131 (see FIG. 1) into spaces formed between the liner 36 and the interior surface of cylinder 34 to produce the full vacuum on the outside of liner 36 and a slightly lower vacuum on the inside of liner 36. The spaces are defined between spacer ribs on the inner surface of the cylinder. This arrangement assures that liner 36 stays fully expanded against the inside wall of tank 34.

The vacuum is also transmitted from source 42 through a multi-port manifold 131 and one or more tubes 44 to one or more suction nozzles 46 to withdraw liquid waste from surgical site 12 when a nozzle is opened. Liquid and other waste from site 12 passes through the nozzle 46, tube 44 and manifold 131 and collects in chamber 39. If the waste liquid level in container 36 reaches float valve 52, the float 52A rises and closes the port to the vacuum connector tube 42, thereby preventing waste liquid from being drawn into the facility vacuum system. The liquid waste collection system will continue to function in the event of a power failure provided that the facility vacuum is maintained.

It is also recognized that during operating procedures, liquids frequently must by removed from the patient irrespective of cauterizing protocols. Such liquids are conducted to the disposable container 39 via tube 44. Each port in manifold 131 is and independent vacuum source. While multiple vacuum lines can be used simultaneously, only one line is shown. Thus, the hospital vacuum is conducted through manifold 33 and tube 44 to the suction nozzle 46. Thus, in this embodiment, waste liquid is drawn down the suction nozzle tube 44 and manifold 33 into container 39.

Liquid waste is withdrawn from container 39 via outlet 54 (at the bottom of cylinder 34) either by pump 56 to the decontamination or sterilizing (treatment) system 40, or, if appropriate, through valve 58 to a non-sterile drain line 58A provided at the user's facility.

In this embodiment, the liquid waste treatment and disposal system 40 utilizes electric power to heat and, thereby, either decontaminate or sterilize the waste steam. The electric power is made available to the complete system 10 through plug 66 which is engaged with a conventional supply of 110 volts at 20 amps or 2200 watts. Local water, preferably at 60–70° F. and in sufficient quantity and pressure, is supplied by the user's facility through water inlet 84. (See also FIG. 1.)

The liquid waste from container 39 is supplied to the treatment and disposal system 40. The system 40 can be programmed to either decontaminate or sterilize waste liquid by selecting the appropriate setting at the control panel 220 as described infra. All other process variables are adjusted automatically to meet the process requirements.

In one embodiment, for example, the system 40 decontaminates the waste stream by raising the temperature thereof to 215° F. for a minimum of 5 seconds. Alternatively, system 40 sterilizes the waste stream by raising the temperature thereof to 290° F. for a minimum of 5 seconds. For convenience hereafter, the decontamination or sterilization system or processes shall be referred to as "treatment" systems or processes.

In the treatment and disposal system 40 shown in FIG. 2, the waste stream is heated to the treatment temperature by one or more passes through heat reservoir 68. This temperature is maintained as the waste stream traverses an insulated tube 74 of the proper length to assure a residence time of at least 5 seconds.

The heat reservoir is, typically, an aluminum (or similar) block which is heated by one or more electrical resistance elements 72 which are able to reach a temperature in excess of 400° F. The waste stream passes from pump 56 to one or more serial passages 74 through the reservoir 68 where the stream is heated to decontamination or sterilizing temperature. The waste stream then passes into residence line 78 made, for example, of stainless steel which provides an adequate residence time for treatment to occur. Temperature sensor 76, for example a thermocouple or the like, disposed at a downstream portion of the residence line 78, is connected to control the pumping speed of waste steam pump 56 to maintain a decontamination or sterilizing endpoint temperature throughout the residence line 78. That is, pump 56 is slowed down if the temperature of the waste material falls below a prescribed temperature.

Downstream pressure regulator valve 79 regulates the pressure in the residence line 78 to maintain the waste stream in a more liquid phase in order to facilitate heat transfer in the reservoir. Typically, the regulator valve 79 can be in the form of an orifice.

The hot (decontaminated or sterile) waste stream passes from the residence line 78 into mixer 82 which is also connected to a water source via conduit 84 and solenoid valve 85. The waste stream is mixed with water in sufficient quantity to reduce the temperature of the combined stream below the legally required temperature of 140° F., which is measured at temperature sensor 92. Thus, after the treatment temperature and time are satisfied, the waste stream is cooled to less than 135° F. by direct contact mixing with water. The combined stream is then discharged into sewer drain 88 via an outlet conduit 86.

Following the removal of some (or all) of the collected liquid waste 48 from container 39, water (or other suitable material) is automatically admitted through the conduit 62 and spray head 64 impinging upon ball 65 or, alternatively, exiting head 64 via lateral slots. Either alternative causes the water to spray uniformly in a horizontal plane, thereby cleaning the walls of the liner 36 as well as flushing waste from the inside of disposable container 39 and from the waste passages of system 40 via pump 56. Typically, the flush water is tap water at 70° F. which is available in an adequate quantity.

After about 1 gallon of water has been sprayed, the water flow through conduit 62 is stopped. This rinse water effectively cleans the container 39 as well as all wetted passages inside the system.

Because of the parameters defined by most surgical procedures, it is desirous to decontaminate 20 liters of waste in about 15 minutes for surgical applications of the invention. The heat reservoir 68 is sized to meet that (or any other) requirement before the temperature of the reservoir falls to a level that makes effective heat transfer possible only at very low flow rates. After the heat reservoir 68 falls below the minimum set point of about 250° F., the block is heated for a new process cycle where-upon a new treatment cycle can be initiated.

Figure 3:
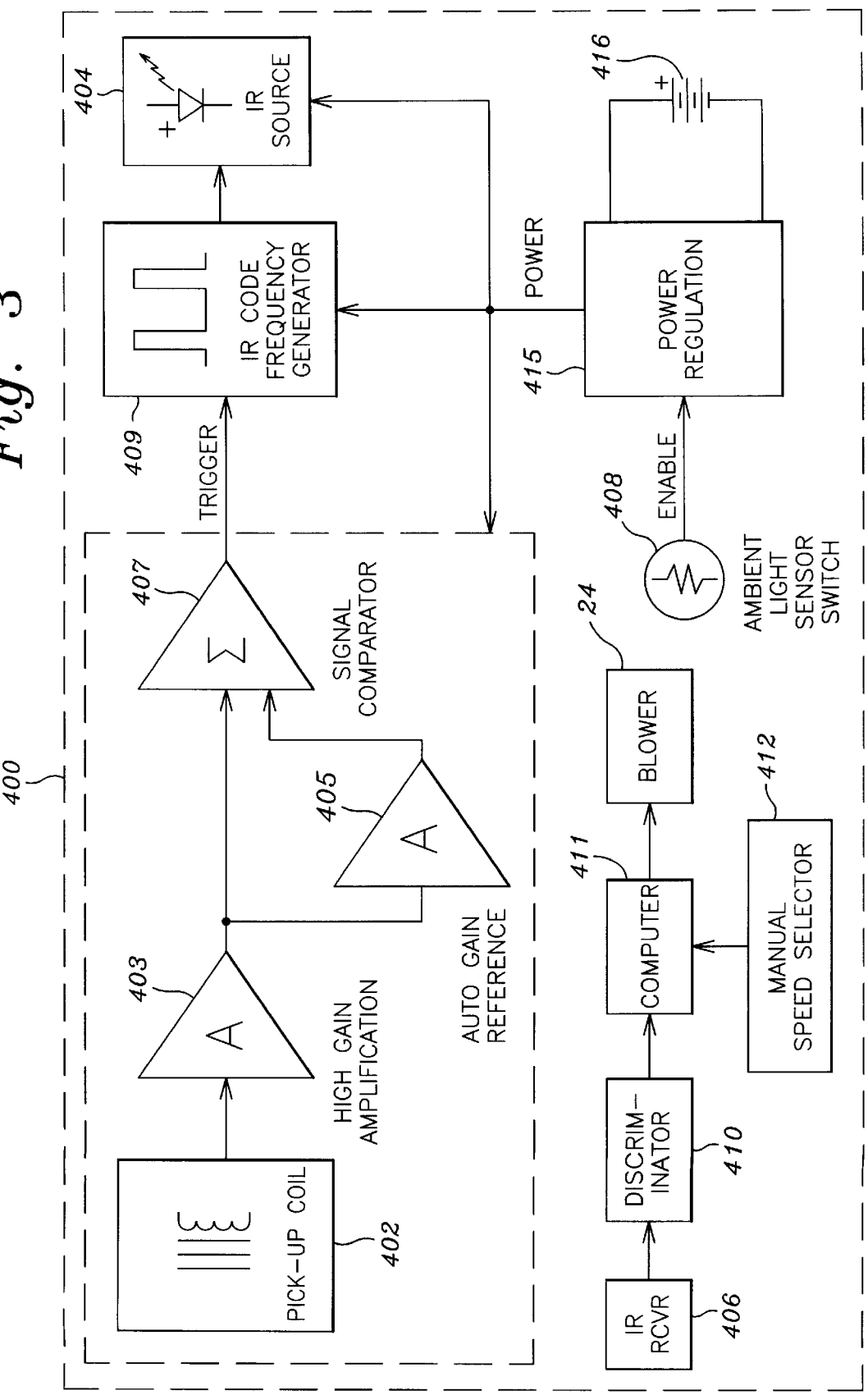
FIG. 3 is a schematic representation of the IR current sensor switch of the instant invention.

Referring now to FIG. 3, there is shown a schematic representation of the IR current sensor switch 400. In particular, a pick-up coil 402 is placed around the existing cautery power cable 26A (see FIG. 1) to sense the current therein. (The power cable need not be altered or modified in any manner.)

In a typical protocol, the cautery machine is activated and a "standby" current exists in the cable. This current (typically based upon a 60 Hz hum in the cable) is supplied to the high gain amplifier 403 which produces an output signal representative of the "standby" current. This signal is supplied to reference amplifier 405 and to one input of comparator 407. The comparator 407 produces a trigger signal which is applied to a frequency generator 409 which produces an IR code frequency signal representative of the "standby" current condition. The IR source 404 produces IR output signals in response to the signal from the generator 409.

When the cautery instrument 26 (see FIG. 2) is turned ON, the current in the cable 26A is sensed by the coil 402 and triggers a coded infra-red (IR) signal from source 404. That is, the high current level in cable 26A is detected whereupon amplifier 403 produces an output signal which is greater (or lesser) than in the "standby" status. This output signal is supplied to amplifier 405 and comparator 407. However, because of circuit delays, the "active" output signal is received first by comparator 407. The comparator 407 then provides a trigger signal to code generator 409 which is different from the "standby" status. Thus, generator 409 supplies a different signal to IR sources 404 which produces IR output signal at a different frequency, as well. This action switches the fan 24 to a relatively higher speed. Conversely, when the cautery instrument 26 is turned OFF, the signal from source 404 correspondingly ceases (or changes) whereupon fan 24 switches back to low speed.

The IR signal produced by source 404 (in each operational mode) bounces off the walls of the operating room (or other locale) until it is picked up by the IR receiver 406, typically, located on control panel 220 of the system. The receiver 406 supplies a signal to discriminator 410 which feeds input data to a computer 411 which determines the speed of fan 24 in the smoke extraction system 20. In one embodiment, the speed of the fan can be manually set or controlled by the manual input 412 represented by a knob 211 in control panel 220 in FIG. 1.

An ambient light sensor 408 detects when the operating room lights are OFF (i.e. the operating room is not in use). The sensor 408 disables the power regulator 415 thereby to disconnect battery 416 and, thus, save transmitter battery power.

Figure 4:
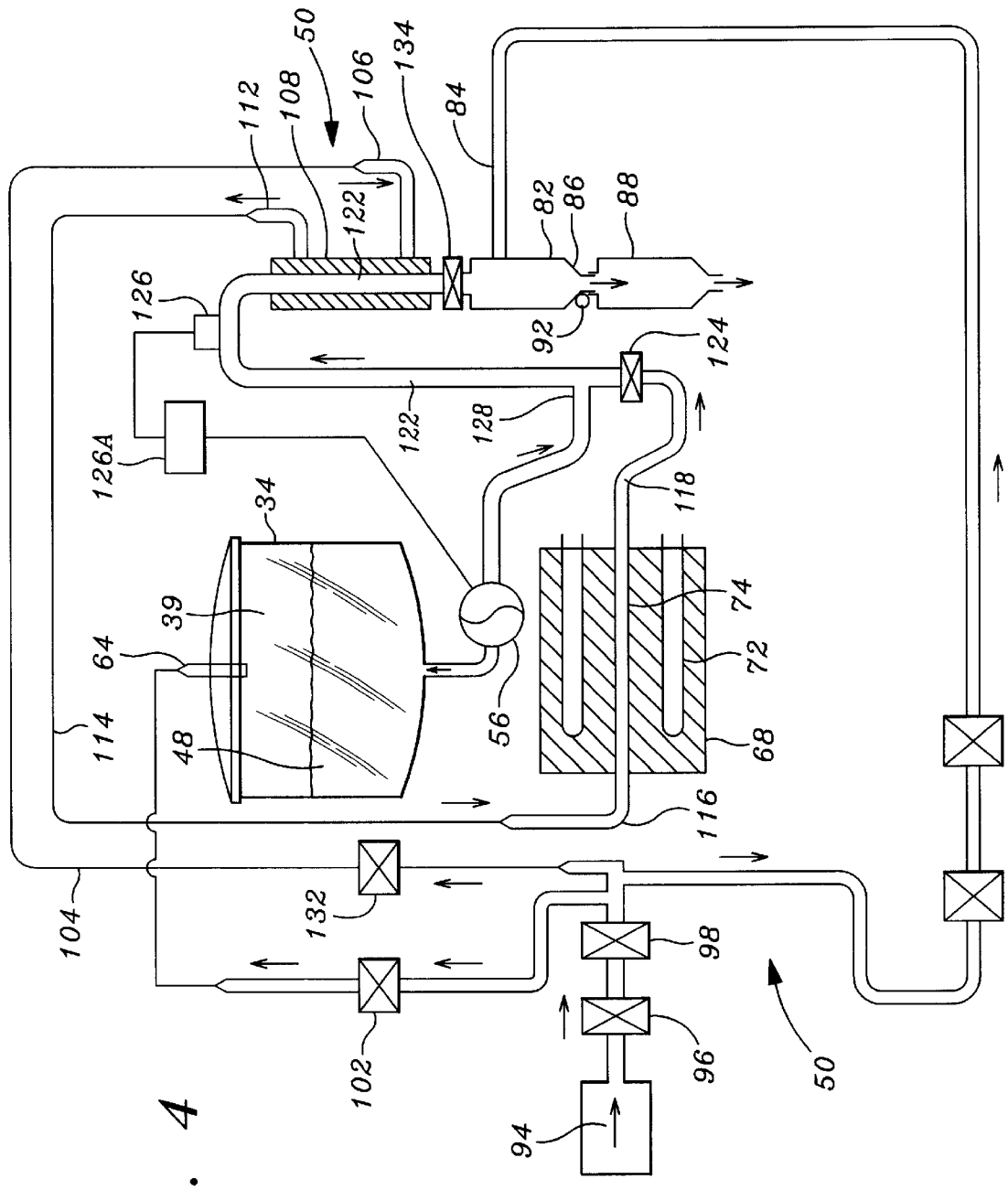
FIG. 4 is a schematic representation of an alternative treatment and disposal system of the instant invention.

Referring now to FIG. 4, there is shown an alternate treatment and disposal system 50 with a desirable heat recovery capability. In this system, components which are similar to components in the system 40 bear similar reference numerals for convenience. Thus, an aluminum (or other suitable) heat reservoir 68 is used to supply heat in system 50. However, in this embodiment, only the water serving as the heat transfer medium passes through channel 74 in heat reservoir 68. Liquid waste is introduced downstream from the reservoir 68 and heated by direct heating (i.e. mixing) with hot water thereby eliminating a potential source of fouling of the heat reservoir. The liquid passages of system 50 are self cleaning by virtue of the automatic steam and hot water flush at the end of each sterilization period.

As shown, water enters system 50 from source 94 (which is similar to source 84 described supra) and passes through check valve 96 which prevents backflow into the water supply. Pressure regulator 98 provides a constant pressure to the system regardless of variations in input water pressure.

Part of the input water is supplied to flushing valve 64 of waste collection tank 34 which is activated at appropriate times by valve 102.

Conversely, the water to be used for treatment heat transfer use passes through flow rate control valve or orifice 132 and tube 104 to the inlet 106 of heat recovery heat exchanger 108. The water then passes through heat exchanger 108 and flows through outlet 112 and tube 114 to the inlet 116 of passage 74 in heat reservoir 68. The water passes through the reservoir 68 where it is heated above the appropriate treatment temperature. The heated water flows through reservoir outlet 118 and back-pressure valve 124 into treatment tube 122. In this arrangement, valve 124 controls the steam-to-water ratio during heating in the reservoir 68 in order to provide-optimum heat transfer from the reservoir to the water stream.

The water stream is supplied to the treatment tube 122 which has an adequate length to assure the required residence time at the treatment temperature described infra. The heated water in tube 122 is then passed through heat recovery exchanger 108 which is, in effect, a jacket which surrounds a portion of the hot water tube 122. Much of the water heat is, thus, transferred to and heats the cool water flowing through heat recovery exchanger 118 from inlet 106 to outlet 112. The water stream is returned from outlet 112 through tube 114 back to the inlet 116 of heat reservoir 68 where the process is continued. Once the operation of the heat and recovery loop is established, the temperature of the water at the inlet 116 to reservoir 68 will be close to the temperature at outlet 118. Thus, only system losses and effective process heat lost when the mixed stream leaves the system needs to be made up by adding heat to heat reservoir 68.

When temperature sensor 126 detects that the proper water temperature for decontamination or sterilizing has been reached throughout sterilization tube 122, pump 56 is activated via a suitable control system 126A, such as a relay switch or the like. Pump 56 begins to pump liquid waste 48 from tank 34 into tube 122 via the entrance 128. As the steam and waste mixture passes through tube 122, temperature sensor 126 and controller 126A control the speed of pump 56 to assure that the decontamination or sterilizing temperature is maintained. The hot, decontaminated or sterile waste and water mixture then passes into heat recovery exchanger 108 where the recovered heat is transferred to the incoming water and then through tube 114 to the inlet 116 of reservoir 68.

The decontaminated or sterile waste stream and water stream then enter mixer 82 via flow control orifice 134 where cool water is introduced via inlet 84. The cool water is supplied in sufficient volume to mix with the waste stream to assure that the temperature of the output stream is below 135° F. as measured by temperature sensor 92. The mixed stream then flows through outlet 86 to sewer drain 88.

Clean water continues to flow through the container 39 and system components, as discussed supra. All parts of the system that contact the liquid waste are flushed in this way. This is accomplished by opening valve 102 to allow water from source 94 to be sprayed into the waste liquid container. The water is supplied at constant pressure and passes through a properly sized orifice to supply a flow a about 0.5 gpm. The flush cycle continues for two minutes. Then all water flow to and from the unit ceases. Pump 56 turns off when the end of a process cycle is reached or tank 34 is empty.

Figure 5:
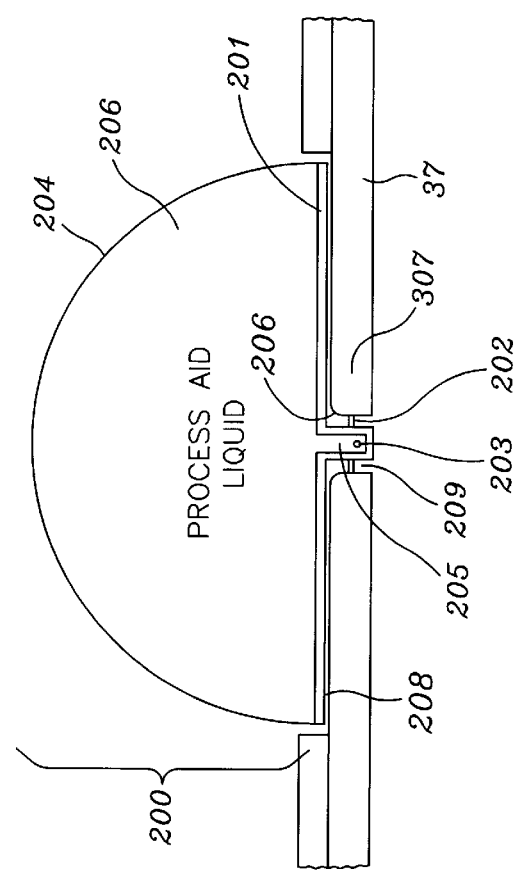
FIG. 5 is a detailed showing of the dispensing system shown in FIG. 2.

Referring now to FIG. 5, there is shown the solution dispenser system 200. This dome-shaped dispenser 204 selectively supplies process aid solution into the waste stream by Venturi action which assures a well mixed and consistent volumetric ratio of process aid solution to waste stream liquid. Dispenser 200 comprises a flexible, dome-shaped container 204 for process aid solution which is hermetically bonded to frame 201. Passages in frame 201 communicate between container 204 and Venturi tube 205 and Venturi holes 203.

That is, the waste stream flows horizontally through a gap 208 between the bottom 201 of dispenser 200 and the upper surface of bottom disc 37. The stream then flows down through the annulus 209 between Venturi tube 205 and a through hole 206 in bottom disc 37. The waste stream accelerates in the annulus 209 thereby generating a reduced pressure in the waste stream proportional to the waste stream velocity which allows the proper amount of process aid solution to be drawn from flexible container 204 through Venturi holes 203 into the waste stream.

Moveable seal 202 moves up and down on Venturi tube 205 sealing Venturi holes 203 in the down position prior to use to prevent inadvertent leakage of process aid liquid. The dispensing system 200 is activated with a brief backflush of water through loop 302 shown in FIG. 6 which forces seal 202 up exposing Venturi holes 203 to the waste stream. The back-flush is stopped and waste liquid begins to flow past Venturi holes 203.

A typical basic process aid aqueous solution 206 may contain, but is not limited to, the following active ingredients, by weight: 1 part sodium carbonate, ½ part tri-sodium phosphate, ½ sodium sulfate. The pH of the concentrated solution is adjusted to assure that, after dilution by the waste stream, the pH is in the 6–10 range when the waste stream is introduced into city drain lines.

Figure 6:
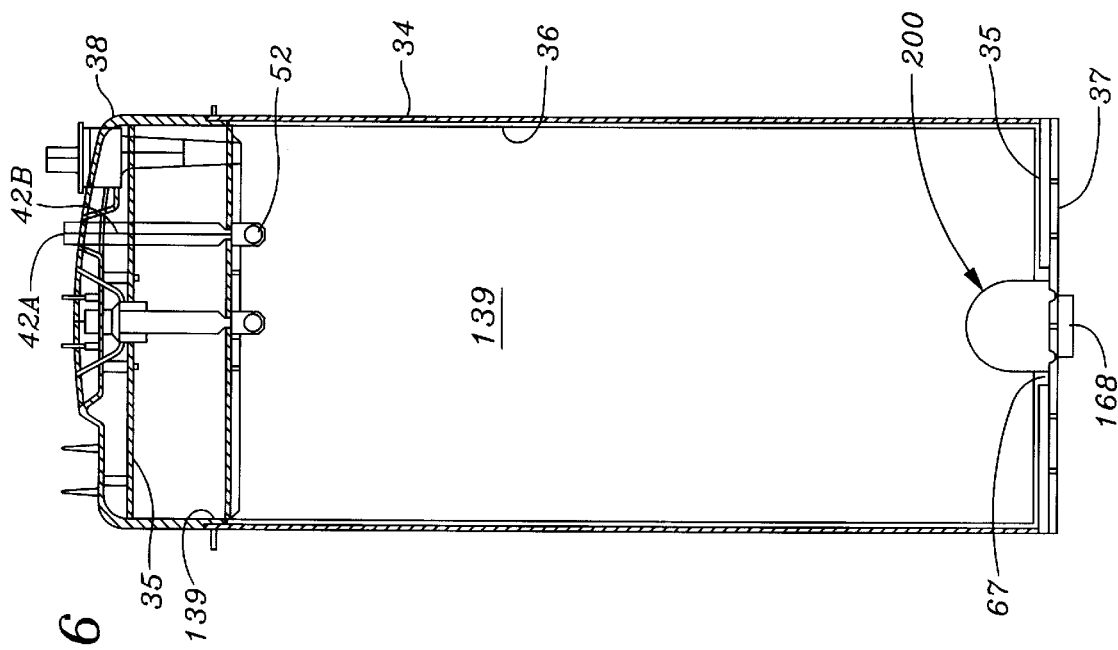
FIG. 6 is a showing of one embodiment of an assembly of the disposable components of the apparatus of the instant invention.

Referring now to FIG. 6, there is shown a more detailed rendering of the liquid waste collection system 30 which includes a waste collection tank 34 which encloses a removable container 139. In a preferred embodiment, the container 139 is constructed to be disposable and may, be convenience, include a tube or cylinder formed of a transparent plastic. The container 139 includes a top 38, a liner 36 sealed thereto, and a bottom disk 37. The top 38 and bottom 37 are made of thermoplastic materials such as ABS plastic and are hermetically bonded to liner 36 which is, typically, formed of a thin film of PVC. The interior of liner 36 and cover 38 defines collection chamber 139.

Tank cover 38 and the fittings bonded to it, tank liner 36, bottom disc 37, coarse filter 35 and dispensing system 200 are disposable and are discarded as a unit.

In a preferred embodiment, a solution dispenser 200 is disposed within container 139. Materials in aqueous solution, e.g. surfactants, may be added by dispenser 200 to the waste stream leaving collection chamber 139 via conduit 54, thereby to prevent fouling of the downstream heat exchanger 40 (or 50) and/or coagulation of organic materials in the waste stream system shown in FIG. 1.

The bottom of the disposable container 139 is fitted with a soft steel element 67 in the form of washer, disk or the like. When the collection container 139 is lowered into the tank 34, a ring magnet 168 in the bottom of the tank attracts the steel ring 67 in the container 139. This attraction force pulls the container bottom down with about 5 lbs. force. Two elastomer seals in the bottom of the tank deform under the 5 lb. force of the container so that continuous contact and a leakproof seal between the container bottom 37 and the interior bottom surface of tank liner 36 is assured. The seals eliminate the chance of liquid leaking laterally along the bottom of tank 34. A coarse filter 35, which filters out particulate matter greater than about 500 microns, is placed on top of the bottom disc 37. This filter prevents large particulates in the waste stream from reaching the pump 56.

The vacuum connector tube 42 passes through a port 42A in cap 38. The port 42A includes and angled orifice 42B which operates to create the vacuum on either side of the liner 36 as described supra.

Thus, there is shown and described a unique design and concept of a medical waste collection and treatment system. The particular configuration shown and described herein relates to such a system which is integrated into a single mobile system. While this description is directed to a particular embodiment, it is understood that those skilled in the art may conceive modifications and/or variations to the specific embodiments shown and described herein. Any such modifications or variations which fall within the purview of this description are intended to be included therein as well.

It is understood that the description herein is intended to be illustrative only and is not intended to be limitative. Rather, the scope of the invention described herein is limited only by the claims appended hereto.

What is claimed is:

1. A waste treatment system comprising, waste receiving means adapted to receive waste material from an activity site, said waste receiving means including a substantially rigid support cylinder and a substantially flaccid waste container which is disposed within said support cylinder, first fluid flow producing means for creating a first fluid flow from said activity site to said waste receiving means whereby the waste material is transported to said waste receiving means, waste treatment means for receiving and treating the waste material received in said waste receiving means to permit ready disposal of the waste material in an environmentally safe manner, and second fluid flow producing means for creating a second fluid flow through said waste treatment means to transport the waste material from said waste receiving means through said waste treatment means.

2. The system recited in claim 1 including, cap means adapted to be mounted at the top end of said support cylinder and to engage and support one end of said waste container.

3. The system recited in claim 1 wherein, said waste treatment means includes a heat exchanger for raising the temperature of said waste material which is passed therethrough to sterilize and/or decontaminate the waste material.

4. The system recited in claim 1 wherein, said first fluid flow producing means includes a blower means connected to said waste receiving means to create a negative pressure in said waste receiving means.

5. The system recited in claim 1, wherein, said second fluid flow producing means includes pump means connected to pump waste material from said waste receiving means to said waste treatment means.

6. The system recited in claim 1 wherein, said first flow producing means includes a waste material carrier liquid which comprises water.

7. The system recited in claim 1 including, a first heat exchanger for raising the temperature of said waste material which is passed through said waste treatment means by said second fluid flow producing means thereby to sterilize and/or decontaminate the waste material.

8. The system recited in claim 7 including, a second heat exchanger for raising the temperature of said second fluid flow producing means prior to passing said waste material through said first heat exchanger.

9. The system recited in claim 8 including, cooling means connected to receive the waste material from said first heat exchanger and reducing the temperature thereof in preparation for disposal.

10. The system recited in claim 8 wherein, said second fluid flow producing means includes a waste material carrier liquid.

11. The system recited in claim 1 including, mobile support means for carrying said waste receiving means, said first and second fluid flow producing means and said waste treatment means as a unitary apparatus.

12. The system recited in claim 1 including, mobile support means for carrying said waste receiving means, said first flow producing means and said waste treatment means as a unitary apparatus.

13. A waste treatment system for receiving and treating waste material to permit ready disposal of the waste material in an environmentally safe manner, comprising, a waste receiver for receiving waste material from an activity site, said waste receiver includes a cylinder which is substantially rigid, and an input device for supplying a carrier material to carry said waste material, a first heat exchanger for raising the temperature of said waste material which is passed therethrough to thereby sterilize and/or decontaminate said waste material, a pump for moving said waste material from said waste receiver to said first heat exchanger, a second heat exchanger for heating the carrier material for transporting said waste through said first heat exchanger, and a preheater for extracting heat from said waste material after passing through said first heat exchanger and applying the extracted heat to the carrier material prior to supplying the carrier material to said second heat exchanger.

14. The system recited in claim 13 including, a pump controller for determining the operational rate of said pump as related to the temperature of said waste material as passed through said first heat exchanger.

15. The system recited in claim 13 wherein, said second heat exchanger includes a heat reservoir mass and a residence line through which said waste material passes in series.

16. The system recited in claim 13 wherein, said pre-heater comprises a jacket assembly mounted at the exterior of said first heat exchanger.

17. The system recited in claim 13 including, a spray head mounted in said waste receiver whereby the interior of said mounting cylinder can be selectively cleansed by emitting a spray of cleaning material.

18. The system recited in claim 13 including, a dispenser of treatment solution mounted in said waste receiver to supply a treatment solution to said waste material which is to be received by said waste receiver.

19. A waste treatment system comprising, waste receiving means adapted to receive waste material from an activity site, first fluid flow producing means for creating a first fluid flow from said activity site to said waste receiving means whereby the waste material is transported to said waste receiving means, waste treatment means for receiving and treating the waste material received in said waste receiving means to permit ready disposal of the waste material in an environmentally safe manner, second fluid flow producing means for creating a second fluid flow through said waste treatment means to transport the waste material from said waste receiving means through said waste treatment means, and a switching device including a current sensor device for selectively activating said first fluid flow producing means.

20. The system recited in claim 19 wherein, said switching device comprises a cautery device.

* * * * *